(12) United States Patent
Crea et al.

(10) Patent No.: US 11,951,143 B2
(45) Date of Patent: Apr. 9, 2024

(54) OLIVE OIL USE

(71) Applicant: Oliphenol LLC, Hayward, CA (US)

(72) Inventors: Roberto Crea, Hillsborough, CA (US); Paolo Pontoniere, Hayward, CA (US)

( * ) Notice: Subject to any disclaimer, the term of this patent is extended or adjusted under 35 U.S.C. 154(b) by 0 days.

(21) Appl. No.: 17/326,146

(22) Filed: May 20, 2021

(65) Prior Publication Data

US 2022/0110989 A1    Apr. 14, 2022

Related U.S. Application Data

(63) Continuation-in-part of application No. 16/854,349, filed on Apr. 21, 2020, now abandoned, and a continuation-in-part of application No. 15/862,413, filed on Jan. 4, 2018, now Pat. No. 11,071,762.

(60) Provisional application No. 63/122,893, filed on Dec. 8, 2020, provisional application No. 62/448,208, filed on Jan. 19, 2017, provisional application No. 62/442,360, filed on Jan. 4, 2017.

(51) Int. Cl.
| | |
|---|---|
| A61K 36/185 | (2006.01) |
| A61K 36/04 | (2006.01) |
| A61K 36/42 | (2006.01) |
| A61K 36/53 | (2006.01) |
| A61K 47/10 | (2017.01) |
| A61K 47/26 | (2006.01) |
| A61K 47/44 | (2017.01) |

(52) U.S. Cl.
CPC ............ *A61K 36/185* (2013.01); *A61K 36/04* (2013.01); *A61K 36/42* (2013.01); *A61K 36/53* (2013.01); *A61K 47/10* (2013.01); *A61K 47/26* (2013.01); *A61K 47/44* (2013.01); *A61K 2236/15* (2013.01); *A61K 2236/35* (2013.01); *A61K 2236/53* (2013.01); *A61K 2236/55* (2013.01)

(58) Field of Classification Search
None
See application file for complete search history.

(56) References Cited

U.S. PATENT DOCUMENTS

| | | | | |
|---|---|---|---|---|
| 2002/0164413 | A1* | 11/2002 | Van Boom | C11B 1/04 426/613 |
| 2014/0010860 | A1* | 1/2014 | Odidi | A61P 25/04 424/463 |

OTHER PUBLICATIONS

ES2512340A1 (machine translation via Google Patents) (Year: 2014).*

* cited by examiner

*Primary Examiner* — Michael Barker
(74) *Attorney, Agent, or Firm* — Rimon P.C.

(57) ABSTRACT

Use of an olive oil milling by-product (Alperujo or Olive Pomace) for the co-processing and co-extraction of natural compounds from medicinal and aromatic plants including cannabis, fruits and agricultural waste, algae and other microorganisms. Separation and stabilization of fractions containing either hydrophilic or liposoluble compounds.

17 Claims, 1 Drawing Sheet

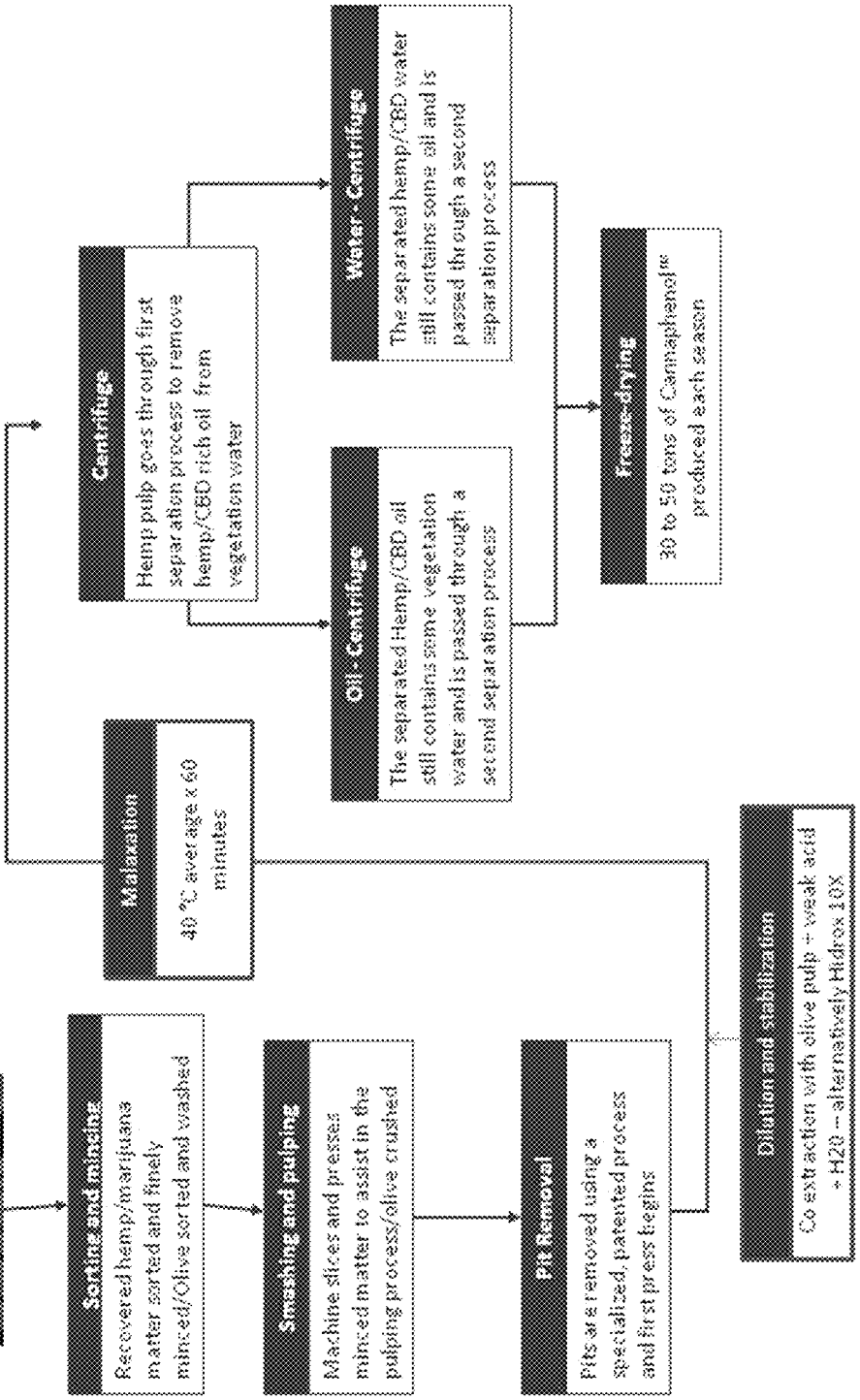
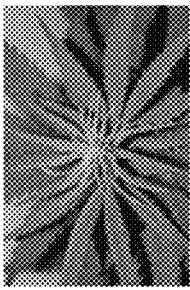

OLIVE OIL USE

CROSS REFERENCE TO RELATED APPLICATIONS

This application is a continuation-in-part of U.S. Non-Provisional application Ser. No. 15/862,413 filed on Jan. 4, 2018 which claims benefit and priority to U.S. Provisional Patent Application No. 62/442,360 filed Jan. 4, 2017 and 62/448,208 filed Jan. 19, 2017; this application is also a continuation-in-part of U.S. Non-Provisional application Ser. No. 16/854,349 filed Apr. 21, 2020; and this application claims the benefit and priority to U.S. Provisional Application No. 63/122,893 filed on Dec. 8, 2020. The disclosures of all of the above-referenced applications are incorporated herein by reference.

SUMMARY

Hemp, a coarse tall plant native of Asia but currently cultivated worldwide, and alternatively called *Cannabis sativa, Cannabis indica*, marijuana or North America Indian hemp, is a genus belonging to Cannabaceac, a small family of flowering plants which includes about 170 species grouped in about 11 genera. It has been used since Neolithic era in its various forms for everything, from commercial products such as clothing, textile, paper, clothing, biofuel, biodegradable plastics, insulating material, paint, food, animal feed, to psychoactive drugs such as marijuana and hashish. Recently discussed for its psychoactive and medical properties the genus *Cannabis* has been at the center of both concerted research efforts, and political and scientific debates. Sought after for the potent resinous glands (trichomes) that grow on the flowers and some leaves (buds) strains such as *Cannabis sativa* and indica have been object of marketing and research effort miring to leverage their healing and recreational attributes. Bred for their content of Tetrahydrocannabinol (THC) and Cannabidiol (CBD), the sativa and indica strains are now being sought after not only for their recreational power but also for applications in health and wellness due their proven efficacy in the management of pain, inflammation, anticarinogenicity and neurodegenerative disease.

While most of the attention has centered around extractive methods meant to isolate cannabinoids bioactives such as THC and CBD, until now little has been done to valorize the full bioactive profile of the plant, and therefore to use extractive methods and applications also for the phytomolecules—mainly polyphenols—that can be derived from the aqueous fraction of the plant and, via water/weak acid and water/ethanol extractive methods (including hydrolysis), and from co-extraction with other kinds of plant biomass.

We present here a process of co-extraction by the use of the pomace fraction of olive oil milling (Alperujo, pomace, etc.) of hemp and hemp fractions like the leaves, the stems and the buds, to enrich an olive oil fraction with liposoluble compounds like THC, CBD1 and 2, and an aqueous fraction containing olive antioxidants with a mixture of natural compounds present in the cannabis plant, The olive matrix is an ideal medium where lipophylic compounds migrate into the oily fraction and hydrophilic compounds end into a stable aqueous fraction respectively.

Experiences carried out with plants with a similar and substantial and valuable lipid component, like for instance *Olea europaea*, have demonstrated that fractions of the plant that were before believed to have no value, either nutritional, medical or commercial are in fact valuable, and can contribute more to human health and wellness than products—such as olive oil in the case of *Olea europaea*—reputed to be (until the introduction of the new methods) the only commercially viable fraction of the plant.

It is well known that both cannabinoids (including THC and CDB) and olive polyphenols possess strong anti-inflammatory, antioxidant, antibacterial and antibiotic properties. Not only that, but studies conducted with both class of bioactives have shown that the application of such bioactives to the management of pain, irritation, wasting phenomena associated with diseases like HIV-AIDS, bacterial infections, and carcinogenesis can produce positive outcomes. Much less is known about the hydrophilic substances, mainly polyphenols, that are produced by the cannabis and lost during the extraction of THC and CBDs.

This invention relates to the use of an olive oil production (olive milling) by-product, called pomace or alperujo, as matrix to co-process plants and fruits or components of them, algae and other microorganisms that contain both hydrophobic and hydrophilic compounds of potential industrial value. This process includes the co-extraction and enrichment of (a) an olive oil fraction with additional liposoluble molecules present in the co-processed product and (b) an enriched water fraction containing soluble molecules in an environment rich of antioxidants provided by the olive vegetation water.

In some embodiments, this invention relates to the use of an olive oil production (olive milling) by-product, called pomace or alperujo, as matrix to co-process cannabis components that contain both hydrophobic and hydrophilic compounds of potential industrial value. This process includes the co-extraction and enrichment of (a) an olive oil fraction with additional liposoluble molecules present in the co-processed product and (b) an enriched water fraction containing soluble molecules in an environment rich of antioxidants provided by the olive vegetation water.

The first step of the process includes the grinding by commercial grinders of a target vegetable tissue or cellular microorganism and the mixing of it with the olive pomace, an agricultural waste product produced abundantly during the olive oil milling. The olive pomace, used in excess (5 to 10 fold w/w), contains an olive oil fraction (2-3%) and an aqueous fraction (60-75%) rich in antioxidants that provide an optimal environment for migration, segregation and stabilization of compounds that belong to the second component, whether a plant, microorganisms, algae and other natural mixtures and that would normally be difficult to separate from their natural matrix. Separation of the light fraction (enriched oil) from the heavy fraction (enriched aqueous fraction) can be obtained by commercial centrifuge (decanters). Optionally the separation is obtained by a 3-phases decanter.

In some embodiments, the first step of the process includes the grinding by commercial grinders of a target cannabis vegetable tissue and the mixing of it with the olive pomace, an agricultural waste product produced abundantly during the olive oil milling. The olive pomace, used in excess (5 to 10 fold w/w), contains an olive oil fraction (2-3%) and an aqueous fraction (60-75%) rich in antioxidants that provide an optimal environment for migration, segregation and stabilization of compounds that belong to the second component, cannabis, whether the buds, the leaves or the stems. Separation of the light fraction (enriched oil) from the heavy fraction (enriched aqueous fraction) can be obtained by commercial centrifuge (decanters). optionally the separation is obtained by a 3-phases decanter.

The process hereby described is a convenient co-extraction that does not necessarily employ any organic solvent for the separation of liposoluble molecules from hydrophilic or water soluble molecules present in a very complex mix, such as in natural plants, tissues and microorganisms.

In some embodiments, the process hereby described is a convenient co-extraction that does necessarily not employ any organic solvent for the separation of liposoluble molecules from hydrophilic or water-soluble molecules present in a very complex mix, such as in the cannabis plant.

BRIEF DESCRIPTION OF THE DRAWING

FIG. 1 illustrates a cannaphenol production method, according to various embodiments of the invention.

DETAILED DESCRIPTION

In the production of olive oil from olives by the modern process of pressing and differential centrifugation, the oil (15-20%) is separated from other components, like the vegetation water (50% of total olive weight) and biomass (5-6% of total olive weight) by the use of commercial decanters. The 3-phases system produces a light fraction (olive oil), a press cake (or insoluble biomass) and a considerable amount of vegetation water (aqueous fraction). The 2-phases decanter, which is mainly used in Spain, Italy and in California, produces the olive oil and a paste-like waste called "alperujo" or "two-phase pomace" or simply "pomace" that has a higher water content (65-80%) and a residual olive oil content of about 2-3%. This is more difficult by-product to treat than the three-phase solid waste and often requires further processing (water evaporation by dryer or percolation) before it can be disposed as solid waste or used for compost or mixed in animal feed.

Usually, the pomace or alperujo is used as fuel in a cogeneration system or as organic fertiliser after a composting operation. Olive mill pomace compost is made by a controlled biologic process that transforms organic waste into a stable humus. Adding composted olive mill pomace as organic fertilizer in olive orchards allows the soil to get nutrients back after each olive crop.

Alperujo or olive pomace is a combination of liquid and solid waste of olive oil processing, being considered dangerous for the environment due to its high content in polyphenols and other organic matter. This by-product does not have common commercial interest, and oil olive companies usually dispose of it in landfills where it can be toxic to the environment. The traditional 2-phases method used in the olive oil industry produces 15-20% oil and 80% waste (alperujo). Introduction of the two-phase centrifugation system for olive oil extraction during the early nineties in Spain has led to the generation of approximately four million tons per year of a solid olive-mill by-product called "alperujo". Alperujo is the main paste produced by the olive oil industry that must be stored in big open-air ponds for months before pomace olive oil is extracted. During this period, malodorous 4-ethylphenol is formed, and it represents a big environmental problem for the oil extracting factories. Agrochemical characterization showed that alperujo has a high moisture content, slightly acidic pH values and a very high content of organic matter, mainly composed by lignin, hemicellulose and cellulose. It also has a considerable proportion of fats, proteins, water-soluble carbohydrates and a small but active fraction of hydrosoluble phenolic substances. It can also be used as mulch after careful composting. The composting process reaches high temperatures which destroys pathogens and weed seeds, breaks down the polyphenols, and converts the organic waste into a stable humus, ready to use in the place of chemical fertilizers. Composting may be considered a suitable alternative for its disposal.

So, when olives are crushed and the first batch of unprocessed extra virgin olive oil is milled out, the resulting alperujo is rich in polyphenols. The polyphenols eliminate the extra electron in free radicals, thus provide potential industrial and health applications. Several processes are available today to recover polyphenols from alperujo or directly from the vegetation water and polyphenols-rich formulations have been proposed to the industry for a variety of health and wellness applications, from skincare to inflammation, benefits in neurodegenerative and cardiovascular diseases. From 1000 kg of alperujo, with 70% humidity, can be obtained approximately 4.5-5 kg of hydroxytyrosol. After a purification process, at least 3 kg of hydroxytyrosol, at 90-95% purity, would be obtained.

The use of alperujo or pomace as such, i.e. as byproduct of a two-phase centrifugation olive oil milling process, for the extraction of valuable natural products from cannabis has apparently never been proposed.

The olive oil byproduct, pomace or alperujo, can be used to co-process and co-extract components of the cannabis plant that contains or produce substances of industrial applications that normally would be separated by expensive chemical means, like extraction by organic solvents or chromatographic processes. We present here the use of alperujo as way to fractionate oil soluble molecules or hydrophobic compounds from hydrophilic compounds normally soluble in the vegetation water.

In addition, the presence of large amount of natural olive antioxidants like hydroxytyrosol or Oleuropein in the pomace and especially in its aqueous fraction will stabilize natural compounds that normally will undergo oxidation by oxygen in the air, whether they are segregated in oil or even better in the vegetation water.

The pomace obtained from two phase olive oil process still contains olive oil (approximately 2-3%) and large amount of antioxidants in form of Oleuropein and hydroxytyrosol. The pomace's composition, as produced by the two-phase decanter process, either further de-pitted or not, therefore represents an optimal matrix to achieve at the same time both separation and stabilization of natural molecules. In addition the separation oil/aqueous fraction that is achieved by a subsequent three phase decanter separation allows the migration and concentration of water soluble compounds in the juice of the olives and the migration/enrichment of the hydrophobic molecules into an oily fraction.

Partitioning of polar molecules in water from molecules that are hydrophobic has been achieved mainly by solvent extraction of aqueous solutions or crude organic matter. That includes the use of organic solvent often in large quantities. Solvent extraction may lead to several drawbacks, including (a) oxidation of the hydrophobic compounds in the presence of oxygen in the air, (b) cost of process, including recovery of the solvent and recycle of it, (c) inefficiency in extraction and emulsion formation.

This presented process is ideal when separation/segregation of naturally occurring compounds by other means are difficult, expensive and inefficient. It facilitates co-extraction of oils that are difficult to separate from natural matrices. The presence of natural antioxidants, like oleuropein and hydroxytyrosol in the olive pomace, in addition, stabilize the natural molecules that are easily oxidized by the air during the process of extraction, separation and storage.

The presence of high concentration $H_2O$ in the aqueous fraction will contribute to separate proteins, and other hydrosoluble compounds for various applications in foods and animal feeds, human dietary supplements and even in the development of botanical drugs.

The aqueous fraction can be dried by water evaporation under vacuum and/or freeze dry process to obtain a powder that can be used in numerous food/feed formulations. Finally, the insoluble biomass, still impregnated with water soluble antioxidants can be stored and used for additional industrial applications.

Examples: we include here an example of co-processing olive pomace with cannabis that will illustrate the process.

Example #1: Co-Processing of Olive Pomace and Algae

Algae are any of numerous groups of chlorophyll containing, mainly aquatic eukaryotic organisms, ranging from microscopic single celled forms to multi-cellular forms 100 feet (30 meters) or more long, distinguished from plants by the absence of true roots, stems, and leaves and by a lack of non reproductive cells in the reproductive structures. They are classified into the six phyla: Euglenophyta, Crysophyta, Pyrrophyta, Chlorophyta, Phaeophyta, and Rhodophyta.

Algae, especially eukaryotic algae are of strong interest in the industry as potential new generation feedstocks for biofuel and other energetic and health applications. Micro algae, like *Nannochloropsis* sp., a unicellular alga, have been genetically engineered to provide fast growing algae that produce large amount of oil. (see, as example O. Kilian and Al., PNAS, Dec. 27, 2011). Other eukaryotic algae, like *Chlamydomonas reinhardii, Chlorella*, (green algae) and/or *Phaeodactylum tricornutum* have been DNA sequenced and used for genetic transformation to increase the production of oil. These species may be grown outdoor and under nitrogen-starvation conditions can accumulate large quantity of oil, sometime exceeding 50-60% of their biomass, on a dry weight basis and provide large quantity of high-quality proteins and oils, including eicosapentaenoic acid (EPA) and other omega 3, and 6 fatty acids endowed with numerous health benefits. Algae are rich in EPA, DHA which are well established long chain fatty acids (omega-3 and omega-6) with proven nutritional and health benefits. Traditional algae oil has been used for the production of biodiesel and jet fuel. Other uses include dietary supplements of omega-3 and omega-6, anti-inflammatory applications, cosmetic and skincare, human consumption in foods, etc.

The separation of the oily fraction from the biomass and proteins has been often cumbersome, expensive and inefficient to the point that the whole technology platform has suffered by the cost of process steps and rendered poorly competitive with respect to other forms of bio-fuel and natural oil extraction.

An inexpensive method of separation of the oil fraction in algae from aqueous compatible fraction is desirable.

Experimental Procedure:

45 kgs dry algae (*Nannochloropsis* sp., kindly provided by Aurora Algae, Inc. Hayward, CA) were submitted to grinding (commercial grinder, Alfa Laval) and directly transported into approx 350 kgs olive pomace (provided by Corto Oil, Lodi, CA) under gentle stirring and at temperature ranging between 25 and 30 C. To the solid slurry mix, approximately 4.0 liters extra virgin olive oil (EVVO) and sufficient amount of hot water (75 C) (20-25 liters) to increase the fluidity of the paste and provide an optimal density suitable for centrifugation by a 3-phase decanter (Alfa Laval). The mixing/kneading process between olive pomace and mechanically ground algae was run for 2 hours at 30 C. The slurry was then pumped into a 3-phases decanter and separation of the oil from the juice/aqueous fraction and biomass obtained by a three-phase decanter. The decanter centrifugation was achieved at 2,700 rpm. Further separation of the oily fraction from residual water was achieved by an additional centrifugation at ca. 7,000 rpm (Alfa Laval vertical centrifuge—F-40 model). Approximately 2.5 gal oil was collected (9.5 liters). The collected oil has the appearance of a dark green color with an intense smell of algae. Its composition in fatty acids is currently subject to further investigation. In addition to the oil, the other two fractions, an aqueous fraction and a solid biomass fraction, were collected separately. Considering that the olive oil pomace yields ca. 0.9%×350=3.15 liters olive oil and another 4.0 were added during the process, the total olive oil fraction in the mix is 7.15 liters. The crude algae oil co-extracted by the above process is therefore approximately 9.5−7.15=2.35 liters (or Kilos. considering an oil Density D=1.0). 2.3 kilos Algae oil from 45 kilos dry algae represents approximately a 5% yield.

The aqueous fraction was collected in a plastic, food grade tote and stored at room temperature in the presence of 1% citric acid.

The biomass or solid fraction is also characterized by a strong odor of algae and was collected separately in plastic bags for further analysis. The biomass could be an ideal fish meal and added to other animal feed and human food supply for its rich residual content in omega-3 fatty acids, olive lipids, proteins, and antioxidants.

Example #2: Co-Processing and Co-Extraction of Carotenoids from GAC Fruit (Mormodica Cochinchinensis)

Carotenoids in nature are responsible for the characteristic colors of various fruits, vegetables and shellfish. Tomatoes and watermelon with red color of lycopene, carrots with orange color of beta-carotene, and dark green vegetables are important sources of carotenoid compounds. The protective effects of carotenoids against various diseases are postulated to be through antioxidant activity, especially in neutralizing pro-oxidant species like ROS and NOS and quenching electrons from free radicals.

GAC fruit (Mormodica Cochinchinensis) a typical fruit of Vietnam that grows in similar subtropical regions of the world, is a perfect combination of a natural red colorant and high beta-carotene content. The inside of GAC contains a fruit meat (yellow) and a red membrane surrounding the seeds. The two fruit components can be separated and analyzed separately for their content in carotenoids. Lycopene is the main component of the red membrane and its concentration is at least 10-fold higher than any other fruit and vegetable of red color. The `GAC fruit also contains high amount of beta carotene, lutein, zeaxanthin polyphenols and beta-cryptoxanthin. Different active phytochemicals are associated with different fruit fractions, like peel, pulp, aril and seeds. These compounds present a different partition coefficient, in that migrate to a liposoluble fraction, like olive oil depending upon their chemical structure or partition in water if their nature is hydrophilic. Thus, an inexpensive and straight forward extraction/co-extraction process that fractionate these phytochemical in two categories, liposoluble compounds and water soluble compounds for the recovery of separate classes of valuable molecules might be highly desirable.

Experimental:

We used ca. 33 kg of minced red melon pulp (inside red membrane) partially depitted to grind finely and mix it to approx. 400 kg olive pomace. The mixture was gently mixed at warm temperature (30-35 C) for about an hour and then separated by a three-phase decanter and vertical centrifuge. We obtained approx 3.5 gal red melon oil+olive oil. The oil is characterized by its bright red color which indicates a migration of lycopene, beta-carotene and other lip compatible compounds into the olive oil. Approximately 4-5 liters olive oil can be expected from the pomace (1%)+2 liters added, while the remaining is accounted for by the co-extracted the red melon oil (ca. 10 liters).

Considering that we started from 33 kg of GAC red membrane and that the total oil collected after centrifugation was approximately 10 liters, the co-extraction process yields approximately a 17% in GAC oil.

Example #3: Co-Processing of Olive Pomace and Aromatic Plants, Rosemary and Lavender Rosemary (*Rosmarinus officinalis*) is an aromatic evergreen plant of the Laminacee plants. Rosemary extracts mainly from the leaves are common herbal products used as flavoring and antioxidant agents used in food processing and cosmetics. The health benefits attributed to rosemary is related to the large number of phytochemical: polyphenols, mainly diterpenoids such as carnosic acid and carnosol; flavonoids and many volatile compound. Up to 57 phytochemical were identified among polyphenols and flavonoids. In order to characterize these products of class of products it would be useful to segregate them into hydrophilic or soluble in water and lipophilic, compounds mainly present in oil and olive oil specifically. Their partition index would/could also help in predicting more beneficial or negative properties, like bioavailability, tissue penetration, accumulation into fats in the body and toxic effects of these properties. An easy co-extraction process that uses olive pomace is in effect a method to separate and identify natural bioactive molecules, otherwise difficult to separate and maintained in their native reduced form. This process could also be used in alternative to solvent extraction which is recognized to have severe limitation when it comes to use the extracted product for food and beverage applications.

30 lbs fresh rosemary leaves, freshly harvested in Mendocino, California (generous gift by Dr. Le Thuy) were submitted to grinding (commercial grinder, Alfa Laval) into fine particles and directly transferred into approx 350 kgs olive pomace (gift by Corto Oil, Lodi, CA) in a kneading tank of approximately 600 liter capacity. The mixture was gently mechanically stirred in the tank at temperature ranging between 25 and 30 C. To the mix we added 5 liters olive oil and sufficient amount of hot water (75 C) (up to 50 liter to increase the fluidity of the paste. The kneading process was run for 2 hours.

The paste was then processed through a three-phase decanter (Alfa Laval-Model 256) and the 3 fractions (oil, juice and biomass) collected separately.

The yield in oil approximate 2.5-3 gallon. (ca. 10 liters). The yield in aqueous liquid is approximately 100 liters, including the added water.

Considering that approx. 5 liters olive oil were added and that 1-2% olive oil is derived from the pomace (3-4 liters), we recovered approximately 1-1.5 liters oil from the rosemary. The yield from rosemary is therefore approx. 10% in oil (i.e. 1 to 1.5 liters from 20 kgs of fresh rosemary).

Similar process was used to extract an oil fraction containing lipophylic pytochemicals present in the flowers of Lavender.

Example #4

45 kgs of cannabis components (leaves, stems, buds, etc.) were submitted to grinding (commercial grinder, Alfa Laval) and directly transported into approx 350 kgs olive pomace (provided by Corto Oil, Lodi, CA) under gentle stirring and at temperature ranging between 25 and 30 C. To the solid slurry mix, approximately 5.0 liters extra virgin olive oil (EVVO) and sufficient amount of hot water (75 C) (20-25 liters) to increase the fluidity of the paste and provide an optimal density suitable for centrifugation by a 3-phase decanter (Alfa Laval). The mixing/kneading process between olive pomace and mechanically ground algae was run for 2 hours at 30 C. The slurry was then pumped into a 3-phases decanter and separation of the oil from the juice/aqueous fraction and biomass obtained by a three-phase decanter. The decanter centrifugation was achieved at 2,700 rpm. Further separation of the oily fraction from residual water was achieved by an additional centrifugation at ca. 7,000 rpm (Alfa Laval vertical centrifuge—F-40 model). Approximately 2.0 gal oil was collected. The collected oil has the appearance of a green color with an intense smell of cannabis. Its composition in fatty acids1 and CBD2 is currently subject to further investigation. In addition to the oil, the other two fractions, an aqueous fraction and a solid biomass fraction, were collected separately.

The aqueous fraction was collected in a plastic, food grade tote and stored at room temperature in the presence of 1% citric acid.

The biomass or solid fraction is also characterized by a strong odor of cannabis and was collected separately in plastic bags for further analysis. The biomass could be an ideal fish meal and added to other animal feed and human food supply for its rich residual content in olive lipids, proteins, and antioxidants.

What is claimed is:

1. A process of coextraction comprising:
   mixing olive pomace with ground cannabis to produce a mixture thereof; and
   separating an aqueous fraction and an oil fraction from the mixture.

2. The process of claim 1 whereby the ground cannabis is first reduced to micro particles by commercial hammer or grinders.

3. The process of claim 1 where liposoluble compounds of the ground cannabis are segregated to the oil fraction and the water-soluble compounds of the ground cannabis are segregated to the aqueous fraction.

4. The process of claim 1 where the aqueous fraction includes hydrophilic compounds of the ground cannabis.

5. The process of claim 1 where separating the oil and aqueous fractions is performed by centrifugation using a three-phase decanter.

6. The process of claim 1 where separating the oil and aqueous fractions is performed by using a two-phase decanter.

7. The process of claim 1 further comprising using a three-phase milling process to produce the olive pomace.

8. The process of claim 1 further comprising using a two-phase milling process to produce the olive pomace.

9. The process of claim 1 where the pomace is first stabilized before mixing by addition of an acid to lower a pH thereof to about 5 to about 2.

10. The process of claim 1 where a weight of olive oil is added to the mixture of olive pomace and ground cannabis in an amount not to exceed 10% of a weight of the pomace in the mixture.

11. The process of claim 1 where the ground cannabis is reduced to 1 to 1000 micron size particles by grinders, hammers or sieves.

12. The process of claim 1 further comprising adding to the mixture an antioxidant.

13. The process of claim 12 wherein the antioxidant is derived from olives.

14. The process of claim 12 wherein the antioxidant is hydroxytyrosol or oleuropein.

15. The process of claim 12 where the antioxidant is added in a concentration ranging from 0.1 M to 10 M.

16. The process of claim 4 wherein the hydrophilic compounds of the ground cannabis include a polyphenol.

17. The process of claim 1 wherein a ratio of olive pomace to the ground cannabis exceeds 5:1 on a weight to weight basis.

* * * * *